United States Patent [19]

Gaffney et al.

[11] Patent Number: 5,698,719
[45] Date of Patent: Dec. 16, 1997

[54] OXIRANE PRODUCTION

[75] Inventors: Anne M. Gaffney, West Chester; C. Andrew Jones, Newtown Square; Rangasamy Pitchai, West Chester; Andrew P. Kahn, Eagleville, all of Pa.

[73] Assignee: Arco Chemical Tehnology, L.P., Greenville, Del.

[21] Appl. No.: 730,692

[22] Filed: Oct. 11, 1996

Related U.S. Application Data

[63] Continuation-in-part of Ser. No. 713,995, Sep. 12, 1996.

[51] Int. Cl.⁶ .................................................. C07D 301/10
[52] U.S. Cl. ...................................................... 549/534
[58] Field of Search ........................................... 549/534

[56] References Cited

U.S. PATENT DOCUMENTS

| | | |
|---|---|---|
| 3,351,635 | 11/1967 | Kollar . |
| 3,888,889 | 6/1975 | Kolombos et al. . |
| 3,962,136 | 6/1976 | Neilsen et al. . |
| 4,007,135 | 2/1977 | Hayden et al. . |
| 4,761,394 | 8/1988 | Lauritzen . |
| 4,766,105 | 8/1988 | Lauritzen . |
| 4,808,738 | 2/1989 | Lauritzen . |
| 4,820,675 | 4/1989 | Lauritzen . |
| 4,833,261 | 5/1989 | Lauritzen . |
| 4,994,589 | 2/1991 | Notemann . |
| 5,011,807 | 4/1991 | Hayden . |
| 5,099,041 | 3/1992 | Hayden et al. . |
| 5,407,888 | 4/1995 | Herzog et al. . |
| 5,504,052 | 4/1996 | Rizkalla . |

FOREIGN PATENT DOCUMENTS

| | | |
|---|---|---|
| 1282772 | 4/1991 | Canada . |
| 1286687 | 7/1991 | Canada . |
| 1286688 | 7/1991 | Canada . |
| 1286689 | 7/1991 | Canada . |
| 1423339 | 2/1976 | United Kingdom . |

OTHER PUBLICATIONS

Doctoral Thesis of Nicholas C. Rigas "Activation of Metal for Ethylene Epoxidation Transient Response Studies on Multicrystalline Powders", Washington University, Sever Institue of Technology, Dec., 1991.

Rigas, N.C. et al. "Transcient Response Studies on the Activation of Silver Metal Surfaces for Ethylene Epoxidation", American Chemical Society, Washington, DC, Aug. 1992.

Park et al. "Ethylene Epoxidation on a Silver Catalyst: Unstead and Steady States Kinetics", J. Catalysis, 105, pp.81–94, 1987.

*Primary Examiner*—C. Warren Ivy
*Assistant Examiner*—Lyma H. Smith
*Attorney, Agent, or Firm*—Stephen D. Harper

[57] ABSTRACT

Oxirane compounds are formed by vapor phase catalytic molecular oxygen oxidation of a $C_3$–$C_{10}$ olefin using a silver catalyst, and the selectivity to the oxirane product is enhanced by preconditioning the catalyst by contact with the olefin at elevated temperature in the absence of oxygen; oxygen is periodically pulsed to the reaction.

8 Claims, No Drawings

OXIRANE PRODUCTION

RELATED APPLICATION

This application is a continuation-in-part of copending application Ser. No. 08/713,995 filed Sep. 12, 1996.

BACKGROUND OF THE INVENTION

1. Field of the Invention

The present invention relates to the catalytic vapor phase molecular oxygen oxidation of an olefin such as propylene to the corresponding oxirane compound using a silver catalyst, and in particular to such a process wherein the catalyst is preconditioned by contact with the olefin in the absence of oxygen.

2. Prior Art

The vapor phase catalytic molecular oxygen oxidation of olefins to oxirane product is well known. Using silver catalysts, this process is the sole commercial process for the production of ethylene oxide. See U.S. Pat. No. 4,766,105, for example.

The technology has been much less successfully applied to the production of propylene oxide. At present the predominant commercial process for propylene oxide production is the catalytic epoxidation of propylene with an organic hydroperoxide. See U.S. Pat. No. 3,351,635. The chlorohydrin process is also practiced commercially.

A substantial amount of work has been done in the field of ethylene oxidation with transient response techniques in order to investigate silver activation. See, for example, the doctoral thesis of Nicholas C. Rigas "Activation Of Metal for Ethylene Epoxidation Transient Response Studies on Multi-Crystalline Powders", Washington University, Sever Institute of Technology, December 1991, "Transient Response Studies of the Activation of Silver Metal Surfaces for Ethylene Epoxidation", N. C. Rigas et al., American Chemical Society, Washington, D.C., August 23–28, 1992, and "Activation of Silver Powder for Ethylene Epoxidation at Vacuum and Atmospheric Pressures", N. C. Rigas etal. See also "Ethylene Epoxidation on a Silver Catalyst: Unsteady and Steady State Kinetics", Park et al., Journal of Catalysis, 105, P. 81–94 (1987).

UK 1,423,339 shows copper catalyzed molecular oxygen oxidation of propylene to propylene oxide characterized in that the catalyst can be given a reductive pretreatment with propylene and thereafter is alternately contacted with propylene/hydrogen and propylene/oxygen mixtures.

A problem with the catalytic vapor phase oxidation of propylene with molecular oxygen as compared with ethylene oxidation has been the generally poor selectivities attainable at any reasonable level of conversion.

BRIEF DESCRIPTION OF THE INVENTION

In accordance with the present invention, it has now been found that in the catalytic vapor phase molecular oxygen oxidation of an olefin such as propylene to the oxirane derivative using a silver catalyst, the reaction selectivity can be markedly improved by first conditioning the catalyst by contact with the olefin in the absence of oxygen followed by rapid introduction of oxygen in reaction concentration.

DETAILED DESCRIPTION

Practice of the invention is especially applicable to the conversion of propylene to propylene oxide. The process is generally useful in the oxidation of olefins having 3–10 carbon atoms with oxidation of alpha olefins having 3–6 carbon atoms being preferred.

Silver catalysts and general reaction conditions which are described in the prior art are useful in carrying out the invention. Supported silver catalysts are especially useful. See for example the teachings of U.S. Pat. Nos. 3,888,889, 4,766,105, 4,820,675, 4,808,738, 4,761,394, 4,833,261, 5,011,807, 5,099,041, 5,407,888, 3,962,136, 4,007,135, 5,504,052, and the like. See also Canadian Patents 1,282, 772, 1,286,688, 1,286,687, 1,286,689, U.S. Pat. No. 4,994, 589. The teachings of all of the above are incorporated herein by reference.

In practice of the invention, it is necessary that the silver oxidation catalyst is first conditioned by contact at elevated temperature, preferably at reaction temperature, with the olefin reactant in vapor form in the absence of oxygen. Generally the time for this conditioning contact ranges from about 10 seconds to about 60 minutes, preferably 2 to 30 minutes. It is especially advantageous to include with the olefin reaction promoters such as halogenated hydrocarbon and/or nitrogen oxide in the conditioning contact. Generally the halogenated hydrocarbon and nitrogen oxide are each incorporated in the feed to the catalyst during conditioning in amount by volume of 10–400 ppm, preferably 50–200 ppm.

After the olefin contact conditioning has taken place, oxygen is incorporated in the feed to catalyst contact as rapidly as possible to bring the oxygen concentration to that to be employed during the main period of reaction. Gradual build-up of oxygen is to be avoided. Surprisingly, it has been found that it is important to avoid gradual oxygen concentration build-up in order to achieve the high selectivities to the product oxirane compound.

After the preconditioning, the oxidation is carried out in the vapor phase by contacting a gaseous mixture of the olefin, e.g. propylene, and a molecular oxygen containing gas, at elevated temperature with the catalyst, eg. by passage through a bed of supported catalyst in the form of granules, discs or pellets.

The amount of olefin in the gaseous mixture can vary within moderately wide limits, for example, between 1 and 90%, preferably between 2 and 20% or between 60 and 80% by volume; care should be taken to avoid the formation of explosive mixtures.

The gaseous reaction mixture preferably contains an inert gaseous diluent or ballast gas, e.g. argon, helium, methane, or nitrogen. The molecular oxygen containing gas is conveniently supplied as air or as high purity oxygen, the latter being preferred. Concentrations of oxygen in the feed range from 5 to 50%. As above described, the gradual build-up of oxygen concentration in the gases fed to catalyst contact is to be avoided. The concentration of oxygen in the gases contacted with the catalyst should be increased from 0% during conditioning to steady state reaction concentration in 10 seconds or less.

The amount of the inert gaseous diluent in the gaseous mixture may vary within the range 0 to 97 preferably 30 to 70% by volume.

The reaction temperature is in the range 100° to 400° C., preferably from 180° to 300° C. The process may be carried out under pressures ranging illustratively from atmospheric to about 20 atmospheres gauge, although higher pressures can be used.

The contact time may be, for example, in the range 0.1 to 60 seconds and preferably is about 2 to 20 seconds.

Various of the additives known for use in such oxidations can be used. Thus, use of very small amounts of chlorinated hydrocarbons such as ethylene dichloride, vinyl chloride, and the like can be used to promote reaction selectivity. Other conventional additives such as nitrogen oxides which promote the reaction can also be used. These additives are preferably contacted with the catalyst along with the olefin during the preconditioning treatment as above described.

After conditioning of the catalyst in the absence of oxygen as above described, followed by rapid introduction of oxygen and production of the oxirane product, high selectivities to the oxirane product are obtained. After a period of such high reaction selectivity, the selectivity declines and the above cycle is repeated.

Generally, after catalyst conditioning, the oxidation reaction is carried out at high selectivity for 10 seconds to one hour, preferably 20 seconds to 30 minutes. Thereafter, at certain intervals the oxygen feed to the reaction is pulsed in order to achieve conditioning of the catalyst and high selectivities upon re-introduction of oxygen.

By "pulsing" in the context of the present invention is meant the periodic decreasing of the oxygen feed rate to the reaction by at least 40% to as much as 100%, preferably by 80 to 100% and most preferably by 100%. The frequency and duration of the oxygen pulses can be varied to achieve optimum performance for a given reaction, but generally the rate of oxygen feed is reduced at least after every 10 seconds to 1 hour of oxygen feed by at least 40% for at-least about 5 seconds, preferably for 10 to 1800 seconds.

In preferred practice, programmed control means are provided to decrease the oxygen feed to the desired extent to the reaction at timed frequency and duration.

In the prior art with regard to propylene oxide production it has been known to periodically discontinue hydrocarbon flow to the reaction for purposes of catalyst regeneration. Thus U.S. Pat. No. 4,007,135 at column 6 line 5 through column 7, line 28 provides a description of prior efforts to produce propylene oxide by vapor phase molecular oxygen oxidation of propylene and at column 7, lines 19–21, states:

"It has been found beneficial in some cases to regenerate the catalyst by exposure to oxidizing conditions for example by interrupting the feed of propylene."

This of course is a teaching which is the converse of the present invention. So far as is known the art does not teach propylene oxide production by vapor phase silver catalyzed procedures which use pulsed oxygen feed, much less suggest that enhanced reaction selectivity is attained by such procedures.

The invention can, perhaps best be illustrated by the following comparison between procedures such as are conventionally employed and the olefin preconditioning and pulsed oxygen feed procedures of the present invention.

CATALYST PREPARATION

A supported silver catalyst is prepared as follows:
Step I
Place a 16 oz. wide mouth jar containing a Teflon-coated stir bar on a stir plate. Add 41.12 g ethylenediamine to the jar, followed by 40.80 g distilled water. Mix well, then slowly add 41.20 g oxalic acid to the jar and allow this to dissolve completely. Slowly add 71.20 g of silver (1) oxide and allow to dissolve completely. Add 14.40 g of ethanolamine and mix well. Add 15.0 g of distilled water and 51.4 g of calcium carbonate. Add 10 mixing stones, cap the jar and ball mill for 4 hours. Dry at 100° C. for 1 hour, then calcine at 300° C. for 4 hours.
Step II
Grind the solids obtained in Step I to a powder. Add 160 ml of distilled water to a 500 ml one-neck round bottom flask. Dissolve 6.2 g potassium nitrate in the water and then add 120 g of ground solids from Step I. Mix for 20 minutes on rotary evaporator, then apply vacuum and heat to 60° C. Continue rotary evaporation until the contents of the flask appear dry. Dry the resulting solids at 110° C. for 2 hours. The resulting catalyst is then pelletized and sieved to 14×30 mesh.

COMPARATIVE EXAMPLE A

A catalyst prepared as above indicated comprising by weight 50% silver and 2% K (KNO$_3$) on Ca CO$_3$ was equilibrated at 250° C. and 2125 Torr by passing through the catalyst at 8250 hr$^{-1}$ GHSV a feed gas comprised by volume of 9.1% propylene, 4.5% oxygen, 91 ppm ethyl chloride, 363 ppm NO, the reminder being argon. At a propylene conversion of 10%, the selectivity to propylene oxide was 30%.

EXAMPLE 1

In accordance with the present invention, the feed oxygen to the reaction was reduced to zero and the composition of the gas fed was adjusted to 12.7% propylene, 254 ppm ethyl chloride and 508 ppm NO, the balance being argon. This feed was passed through the catalyst at 5910 hr$^{-1}$ GHSV, conditions of temperature and pressure were 250° C. and 2211 Torr. After 20 minutes at these conditions, oxygen was pulsed into the feed for 20 seconds to give an oxygen concentration in the feed of 20 vol % in less than 1 second. During the 20 second oxygen pulse, reaction selectivity of the conversion of propylene to propylene oxide increased to 61.5%.

Oxygen feed was discontinued for 6 minutes and then pulsed into the feed for an additional 20 seconds to give 20% by volume oxygen in the feed as above at the above conditions. During this pulse, selectivity of the conversion of propylene to propylene oxide rose to 54.4%.

CATALYST PREPARATION

The following were combined in a 4 oz jar with 5 ceramic stones: ethylene diamine (10.30 g), distilled water (10.20 g), oxalic acid dihydrate (7.50 g), silver(1) oxide (13.0 g), ethanolamine (3.63 g), potassium nitrate (1.59 g) in distilled water (5.17 g), and calcium carbonate (17.0 g). The jar was sealed and placed on a ball mill for 4 hours. The mixture was dried at 110° C. for 1 hour. The temperature was then ramped at 10° C./min to 300° C. and held for 3 hours. The resulting catalyst was pelletized and sieved to 14×30 mesh.

COMPARATIVE EXAMPLE B

Catalyst prepared as above comprising by weight 40% Ag and 2% K on CaCO3 was equilibrated at 250° C. and 40 psig by passing through the catalyst at 1200 hr$^{-1}$ GHSV a feed gas comprised by volume of 10% propylene, 5% oxygen, 200 ppm NO, 50 ppm ethyl chloride, the remainder being nitrogen. At a propylene conversion of 14%, the propylene selectivity to propylene oxide was 34%.

EXAMPLE 2

After running the conditions of the Comparative Example B above, the feed oxygen to the reaction was reduced to zero and the composition of the gas feed was adjusted with nitrogen to maintain a GHSV of 1200 hr$^{-1}$. After 30 minutes at these conditions the oxygen was returned to the feed the composition of which was adjusted to that in the above Comparative Example B, at which time the selectivity of the conversion of propylene to propylene oxide rose to 44%.

These results illustrate the surprising and important improvement achieved by preconditioning the silver catalyst by contact with propylene at elevated temperature. The results also show the dramatic improvements achieved by the pulsing of oxygen in accordance with the invention as compared to conventional oxidation procedures.

We claim:

1. In a continuous process for the production of an oxirane compound by the catalytic vapor phase molecular oxygen oxidation of an olefin having 3–10 carbon atoms in the presence of a silver catalyst, the improvement which comprises conditioning the silver catalyst by contact with an oxygen free vapor feed stream comprised of the olefin at elevated temperature, and thereafter contacting the conditioned catalyst at reaction conditions with a feed stream comprised of olefin and oxygen.

2. The process of claim 1 wherein oxygen is periodically pulsed to the reaction.

3. The process of claim 1 wherein the olefin is an alpha olefin having 3–6 carbon atoms.

4. The process of claim 1 wherein the olefin is propylene.

5. The process of claim 1 wherein the said oxygen free vapor feed stream is comprised of halogenated hydrocarbon and/or nitrogen oxide.

6. The process of claim 1 wherein the oxygen concentration is increased from 0% to reaction concentration in 10 seconds or less.

7. The process of claim 1 wherein the catalyst is conditioned for 10 seconds to 60 minutes between oxygen pulses.

8. The process of claim 1 wherein each oxygen pulse is for 10 seconds to 1 hour.

* * * * *